United States Patent [19]

Glaser et al.

[11] Patent Number: 4,523,769

[45] Date of Patent: Jun. 18, 1985

[54] WHEELCHAIR AND DRIVE SYSTEM THEREFOR

[75] Inventors: Roger M. Glaser, Dayton; Jerrold S. Petrofsky, Beavercreek; Howard R. DuFour, New Carlisle, all of Ohio

[73] Assignee: Wright State University, Dayton, Ohio

[21] Appl. No.: 417,933

[22] Filed: Sep. 14, 1982

[51] Int. Cl.³ .......................... A61G 5/02; B62M 1/04
[52] U.S. Cl. .......................... 280/252; 3/1.1; 128/421; 74/105; 74/128; 74/143; 180/6.5; 280/242 WC; 297/DIG. 4
[58] Field of Search .............. 280/252, 242 WC, 7.15, 280/289 WC, 249; 180/6.5, DIG. 3; 297/DIG. 4; 74/128, 105, 143; 128/25 R, 80 R, 421, 422, 423 W; 3/1.1

[56] References Cited

U.S. PATENT DOCUMENTS

| | | | |
|---|---|---|---|
| 98,819 | 1/1870 | Wanner | 280/252 |
| 531,330 | 12/1894 | Potter | 280/211 |
| 2,210,269 | 8/1940 | Taylor | 280/242 WC X |
| 2,397,790 | 4/1946 | Kapusta | 74/143 |
| 3,374,845 | 3/1968 | Selwyn | 180/6.5 |
| 3,463,146 | 8/1969 | Schwartz et al. | 128/25 R |
| 3,588,144 | 6/1971 | Padial | 280/252 X |
| 3,814,199 | 6/1974 | Jones | 180/6.5 |
| 3,989,240 | 11/1976 | Victor et al. | 272/125 |
| 4,078,627 | 3/1978 | Brown et al. | 180/6.5 |
| 4,284,157 | 8/1981 | Lay | 180/65 R |
| 4,421,336 | 12/1983 | Petrofsky et al. | 280/252 |

FOREIGN PATENT DOCUMENTS 2227851 11/1974 France ..................... 280/242 WC
343810 10/1936 Italy ....................... 280/200

Primary Examiner—Joseph F. Peters, Jr.
Assistant Examiner—Mitchell J. Hill
Attorney, Agent, or Firm—Biebel, French & Nauman

[57] ABSTRACT

A wheelchair includes a chassis, a pair of side wheels for supporting and driving the chassis, at least one front wheel for cooperating with the side wheels in supporting the chassis, and a seat mounted on the chassis for supporting the body of a disabled person. A pair of individually moveable footrests support the feet of the person. A driving gear is mounted for rotation concentrically and in conjunction with each of the side wheels, and a lever is pivotally mounted for rotation concentric with but independent from each of the driving gears. A pawl is mounted on each of the levers for engagement and disengagement with the corresponding driving gear. A pivoted arm and a series of rods connect each lever and pawl with one of the footrests, such that movement of the footrest by the leg of the disabled person in one direction causes the pawl to engage the driving gear and the lever to drive the gear for propelling the wheelchair. Movement of the footrest in the opposite direction causes the pawl to disengage and the lever to return to its original position. The disclosed wheelchair may be adapted such that the legs of a paralyzed individual can propel the chair through use of electrical muscle stimulation.

13 Claims, 8 Drawing Figures

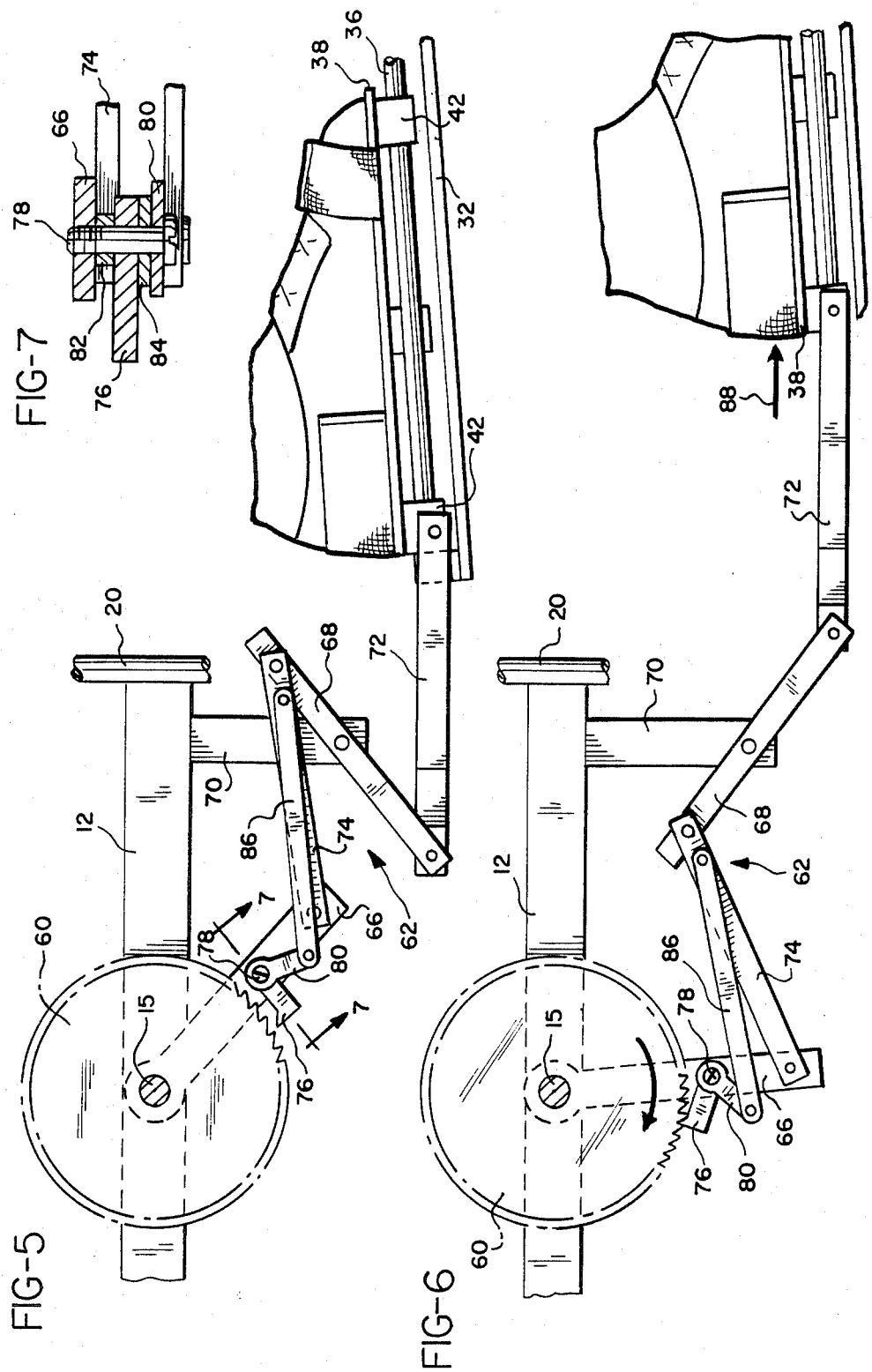

WHEELCHAIR AND DRIVE SYSTEM THEREFOR

BACKGROUND OF THE INVENTION

The present invention relates to a wheelchair, and more particularly, to such a wheelchair that is adapated to be driven by action of the legs of the occupant thereof.

Disabled individuals frequently use manual wheelchairs, often powering them by rotating the large wheels of the chair with their arms. This form of locomotion is quite stressful, however, due to the use of the relatively small and weak upper body musculature. In addition, decreased physical activity due to non-use of the muscles of the lower body can often lead to health problems such as poor circulation, cardiovascular disease, and the loss of calcium from bones, which then become vulnerable to fractures.

Many persons are confined to wheelchairs for reasons other than paralysis of the legs or lower body. For example, the person may be incapable of maintaining balance when in a standing position or, due to age or some other cause, may lack the necessary strength for walking. In addition, while a person may suffer paralysis, it may be limited to one leg or a portion thereof. For such persons, it would be highly beneficial to be able to make use of the muscles of the legs and lower body, to the extent they may be capable, in propelling themselves about in wheelchairs.

Additionally, as is disclosed in U.S. Pat. No. 4,421,336 issued Dec. 20, 1983 to Petrofeley et al., it has been discovered that in many cases of lower limb paralysis, it is possible to use electrical stimulation to cause the muscles of the paralyzed limbs to operate in controlled fashion. In most cases of lower limb paralysis, the motoneurons from the spinal cord to the skeletal muscles of the legs, as well as the muscles themselves, are functional. Reasons for the paralysis are usually due to loss of neuronal connections or function between the brain and the motoneurons which leave the spinal cord. If the motoneurons or the paralyzed muscles are stimulated directly by an electrical stimulator, muscular contraction will occur.

It would appear from this discovery that in the case of paralyzed individuals, the health benefits discussed above could be achieved by utilizing electrical stimulation of the leg muscles to aid in propulsion of the individual in a wheelchair.

What is needed, therefore, is a wheelchair which includes provision for propulsion by the legs of the chair occupant. Such a wheelchair could be driven in whole or in part through the use of the muscles of the legs and lower body, and could be adapted for use in conjunction with electrical muscle stimulation.

SUMMARY OF THE INVENTION

A wheelchair includes a chassis, a pair of side wheels for supporting the chassis, at least one front wheel for cooperating with the side wheels in supporting the chassis, and a seat mounted on the chassis for supporting the body of a disabled person. A pair of individually movable footrests are provided for supporting the feet of the person, the footrests operating to generate linear motion in response to extension and flexion of at least one of the lower legs of the person. Drive means connected to the footrests translate the linear motion into rotary movement for propelling the wheelchair.

The drive means may include a pair of driving gears, one gear being mounted for rotation concentrically and in conjunction with each of the side wheels. Means for engaging each of the driving gears is provided for individual driving movement of the gears in a first rotational direction, and for non-engaging individual movement along the driving gears in a second rotational direction opposite the first direction. Additional means connects the engaging means with the footrests, such that individual movement of one of the footrests in a first linear direction causes the engaging means to move one of the driving gears in the first rotational direction, and movement of the footrest in a second linear direction opposite the first linear direction causes movement of the engaging means in the second, non-engaging rotational direction.

The engaging means may include a pair of levers, each of the levers being pivotally mounted for rotation concentric with but independent from one of the driving gears. A pawl is pivotally mounted on each of the levers, and a pair of means pivotally moves each pawl for engagement with the corresponding one of the driving gears in response to movement of the lever carrying the pawl in the first rotational direction, and for disengagement from the gear in response to movement of the lever in the second rotational direction.

The means connecting the engaging means with the footrests may include a pair of connecting assemblies, each of the assemblies including an arm pivotally mounted to the chassis at a point along the arm remote from either end thereof. A first rod is pivotally connected between a first end of the arm and one of the footrests, and a second rod is pivotally connected between the end of the arm opposite the first end and one of the levers. Movement of the footrest in the first linear direction causes the first rod to pivot the arm in one direction, the second rod thereby moving the lever in the first rotational direction. Conversely, movement of the footrest in the second linear direction causes the first rod to pivot the arm in the opposite direction, the second rod thereby moving the lever in the second rotational direction.

Each of the means for pivotally moving one of the pawls may include a third rod pivotally mounted at one end thereof to the second rod. A linkage is pivotally connected to the end of the third rod opposite the one end, and is further pivotally mounted to the lever at the point of mounting of the pawl. A friction pad is disposed between the pawl and the linkage, with the third rod, the linkage and the friction pad being operative to pivot the pawl into engagement with the driving gear in response to pivotal movement of the arm caused by movement of the footrest in the first linear direction, as well as to pivot the pawl out of engagement with the driving gear in response to pivotal movement of the arm caused by movement of the footrest in the second linear direction.

Accordingly, it is an object of present invention to provide a wheelchair that may be propelled by the legs of the chair occupant; to provide such a wheelchair that is readily adaptable to propulsion by electrical stimulation of the legs of a paralyzed occupant; to provide such a wheelchair that can obtain for the user various health benefits derived from use of the lower body musculature; and to provide such a wheelchair that, although adapted for propulsion by the legs of the occupant, may be moved in more traditional fashion, such as by the arms of the chair occupant or by pushing of the chair by a second person.

Other objects and advantages of the present invention will be apparent from the following description, the accompanying drawings, and the appended claims.

BRIEF DESCRIPTION OF THE DRAWINGS

FIG. 5 is an elevational view showing in detail the drive system and its operation;

FIG. 6 is a view similar to FIG. 5 showing further the operation of the drive system;

FIG. 7 is a view taken generally along line 7—7 in FIG. 5; and

DETAILED DESCRIPTION OF THE PREFERRED EMBODIMENTS

Figure 1:
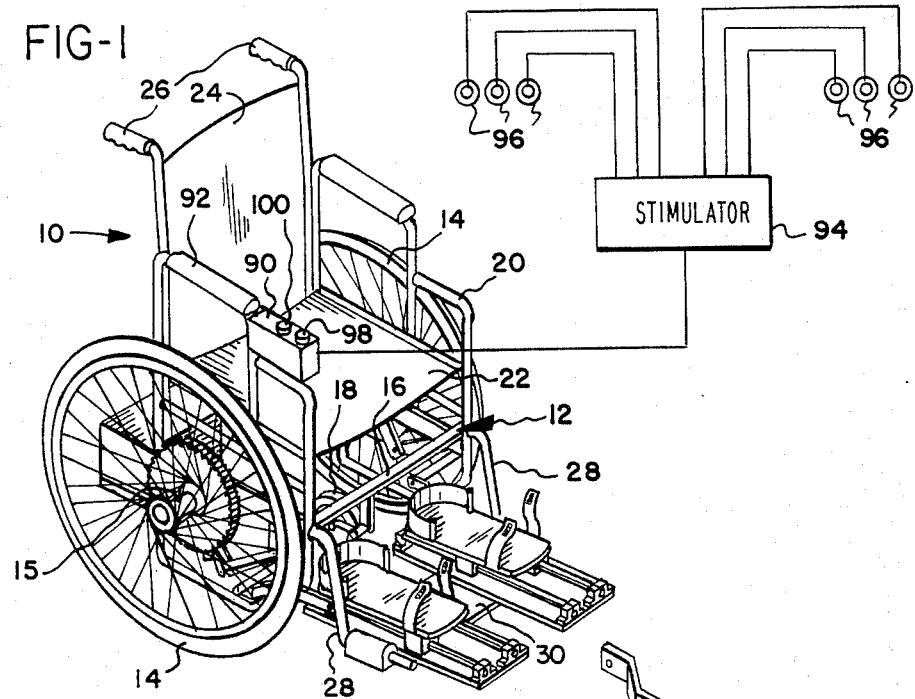
FIG. 1 is a perspective view showing generally the wheelchair of the present invention, along with a schematic representation of a circuit for providing electrical stimulation to the legs of a paralized chair occupant.

Referring now to FIG. 1, the wheelchair 10 of the present invention includes a chassis 12 to which is rotatably mounted a pair of relatively large side wheels 14, each on one of a pair of axes 15. Chassis 12 includes crossmember 16, having pivotally mounted thereto a smaller front wheel 18. To the chassis 12 is connected the chair frame 20, which in turn carries the seat 22 and back 24 of the wheelchair 10. The frame 20 additionally includes a pair of handles 26, enabling the wheelchair 10 to be pushed from behind.

Figure 2:
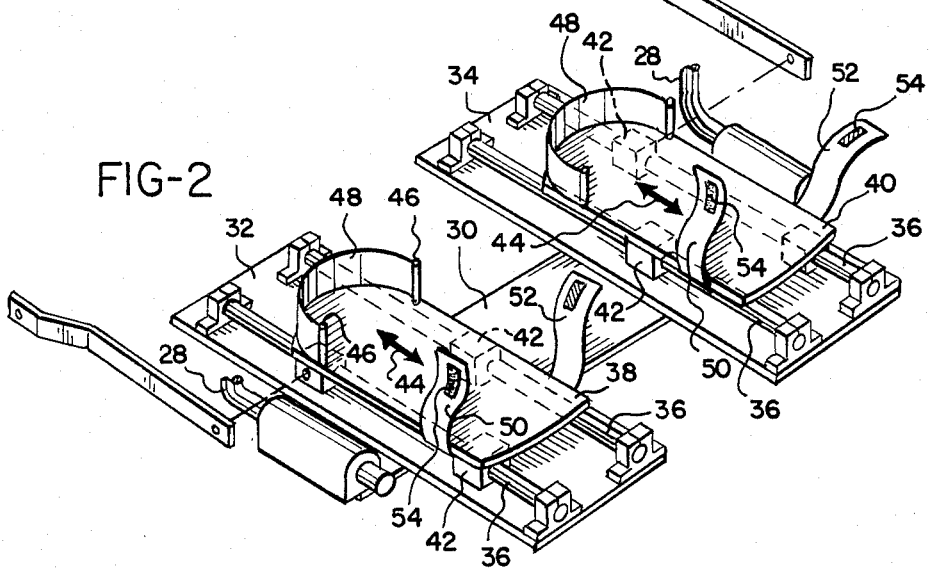
FIG. 2 is a perspective view showing in greater detail the footrests of the wheelchair.

The chair frame 20 further includes a pair of members 28 that extend forwardly from the wheelchair 10 and carry at the ends thereof a foot support platform 30. As seen in FIG. 2, a pair of support plates 32 and 34 are attached to the platform 30, with each including a pair of rods 36 mounted in parallel along the length of plates 32 and 34. Rods 36 are each held in place by a pair of mounting blocks 37, so that a clearance is provided between rods 36 and plates 32 and 34. A pair of footrest 38 and 40 each have three linear ball bearing assemblies 42 mounted to the bottoms thereof, arranged with two of the bearing assemblies 42 toward one side and one toward the other side of each of the footrests 38 and 40. The bearing assemblies 42 in turn ride upon the rods 36 mounted to plates 32 and 34, so that footrests 38 and 40 are carried by plates 32 and 34, respectively, and may be moved therealong in a back and forth manner as indicated by arrows 44.

Each footrest 38 and 40 includes a pair of upwardly projecting posts 46 mounted near the rear end thereof. A flexible heel strip 48 is connected between posts 46, preferably constructed of a material such as nylon webbing, canvas or the like. Each footrest 38 and 40 further includes a pair of toe straps 50 and 52, constructed of the same material as heel straps 48, mounted near the forward end of each footrest. A fastening means, preferably a cooperating pair of Velcro ® strips is included for fastening the ends of toe staps 50 and 52.

Figure 3:
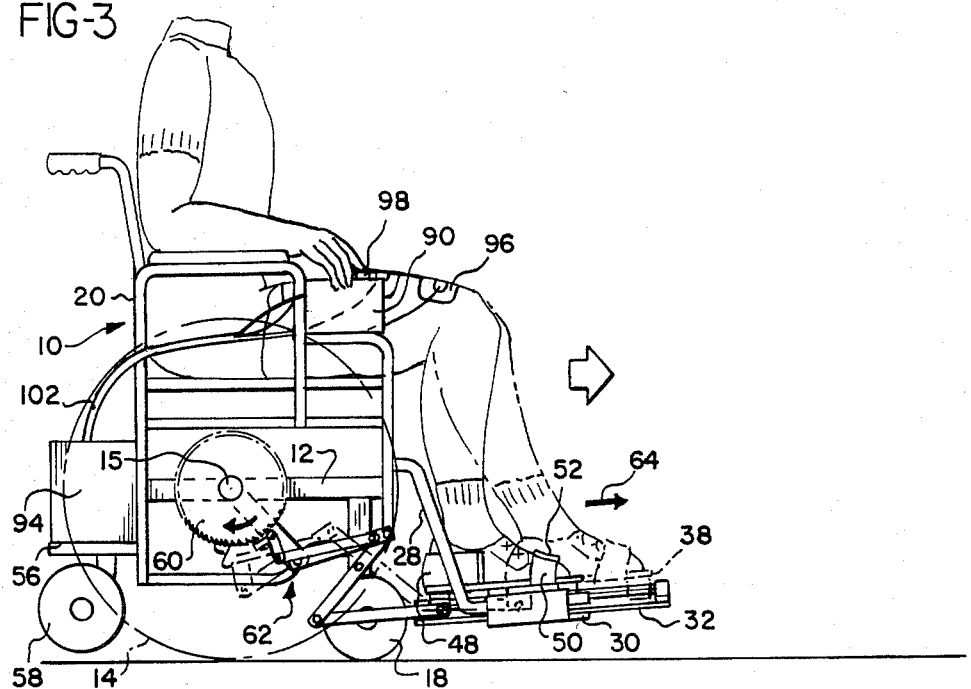
FIg. 3 is an elevational view showing generally the operation of the wheelchair.

The placement of a foot of the occupant of the wheelchair 10 on footrest 38 may be seen by reference to FIG. 3. The heel is placed into the curvature of heel strap 48, and the toe straps 50 and 52 are fastened over the toes of the foot. Of course, it will be recognized that placement of the other foot of the chair occupant upon footrest 40 is identical.

In addition, from FIG. 3 it will be noted that the mounting of footrest 38, and thus of footrest 40 as well, is such that the footrests define a slight angle with respect to the ground so that the travel path of the footrests slope upwardly away from the wheelchair 10. The slope is provided to accommodate the upward movement path of the foot as the lower leg is extended, as well as to facilitate operation of the wheelchair 10 by the leg muscles, as will be described below.

The wheelchair 10 further includes a frame portion 56 extending rearwardly from the main section of frame 20. A rear wheel 58 is attached to frame portion 56, but as can be seen from FIG. 3, wheet 58 is normally not in contact with the ground. Wheel 58 is provided so as to serve as a safety stop in the event wheel chair 10 should fall backwards.

Figure 4:
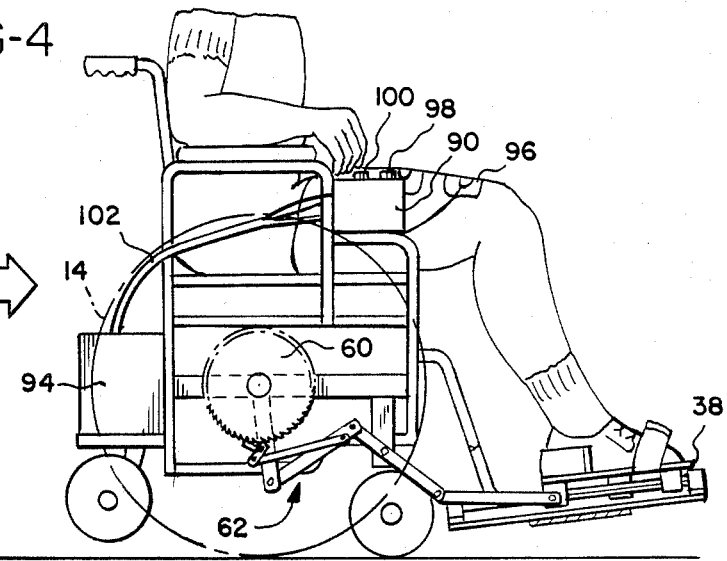
FIG. 4 is a view similar to FIG. 3 showing further the operation of the wheelchair.

The operation of the wheelchair 10 for propulsion by the legs of the chair occupant may be seen generally in FIGS. 3 and 4. A pair of drive gears 60 (only one shown) are mounted adjacent each wheel 14, attached to the same axles 15 supporting the wheels. Each gear 60 rotates in conjunction with the associated wheel 14. A drive means 62, described in greater detail below, is connected between each of the footrests 38 and 40 and a corresponding one of the drive gears 60. To propel the wheelchair 10, one or both of the legs of the chair occupant is extended as shown by arrow 64. The drive means 62 then operates to translate the linear motion of the footrest 38 or 40 into rotary movement for driving the gear 60, and in turn drives the wheelchair 10. Once the leg is extended to the degree remitted by footrest 38 or 40, as seen in FIG. 4, it may be retracted, during which time the drive means 62 becomes disengaged from the gear 60 and returns to its starting position.

The details of the construction and operation of the drive means 62 may be seen by reference to FIGS. 5 and 6. A lever 66 is mounted to the axle 15 supporting driving gear 60 (as well as side wheel 14), but is mounted for pivotal rotation independent from rotation of gear 60 and wheel 14. An arm 68 is pivotally mounted near the center thereof to a depending projection 70 of chassis 12. Pivotally connected to one end of arm 68 is a rod 72. The other end of rod 72 is pivotally mounted to the rearward-most bearing assembly 42 on footrest 38, so that movement of footrest 38 also moves rod 72. A second rod 74 is pivotally connected between the other end of arm 68 and the outermost end of lever 66.

A pawl 76 is pivotally mounted to lever 66 near the outer edge of driving gear 60 for engagement of pawl 76 with gear 60. Pawl 76 is attached by a bolt 78 or the like, which also pivotally connects a linkage 80 to lever 66. As seen in FIG. 7, a spacer 82 is placed on bolt 78 between lever 66 and pawl 76, and a friction pad 84 is disposed on bolt 78 between pawl 76 and linkage 80. Linkage 80 is further pivotally attached to one end of a third rod 86, the other end of rod 86 being pivotally attached to rod 74.

For operation, the drive means 62 is initially positioned as shown in FIG. 5. Extension of the lower leg results in movement of footrest 38 as indicated by arrow 88 in FIG. 6, which carries rod 72 in the same direction.

Movement of rod 72 results in pivotal motion of arm 68, whereby rod 74 is moved linearly in a direction opposite that of rod 72. In turn, lever 66 is rotated in a driving direction about driving gear 60.

Lateral movement of rod 74 causes similar movement of rod 86, which rotates linkage 80 about bolt 78. The rotary motion of linkage 80 is transmitted to pawl 76 through friction pad 84, causing pawl 76 to engage the teeth of driving gear 60. Thus, the rotary motion of lever 66 about its axle 15 rotates gear 60, which in turn rotates side wheel 14, driving the wheelchair 10 forward.

Upon complete extension of the leg to the degree permitted by footrest 38, drive means 62 is halted in the position indicated in FIG. 6. Cessation of linear motion of rod 86 and rotational motion of linkage 80 about bolt 78 results in removal of the driving force from pawl 76, which thus drops from engagement with driving gear 60 to a disengaged position where it is held in place by friction pad 84. Movement of the footrest 38 is then begun in the opposite direction, which may be performed solely by gravity due to the slight slope of the footrest assembly, or may be assisted by flexion of the leg muscles. In any event, return motion of footrest 38 causes rod 72 to pivot arm 68 in the opposite direction, whereby rod 74 rotates lever 66 about axle 15 also in the opposite direction.

Since pawl 76 is not longer engaged, rotation of lever 66 has no effect upon driving gear 60, and the wheelchair 10 is not moved in any direction. Once the footrest 38 is returned to its original position, the drive means 62 is again ready for driving of wheelchair 10.

It will, of course, be recognized that a mirror-image drive means 62 is mounted to the wheelchair 10 on its other side, connecting the footrest 40 with the other driving gear 60 and side wheel 14, and operating in a manner identical to that described above.

Since each side wheel 14 may be rotated freely at all times except during the driving movement of the associated footrest 38 or 40, due to the disengagement of the pawls 76 from gears 60, the wheelchair 10 may be operated in a number of different ways. It can be propelled entirely by the legs of the wheelchair occupant, in which case the occupant's legs may be extended and retracted either in alternating fashion or simultaneously. The wheelchair 10 may be moved by a combination of use of the occupant's arms and legs. Additionally, the wheelchair can be pushed from behind by a second person.

Figure 8:
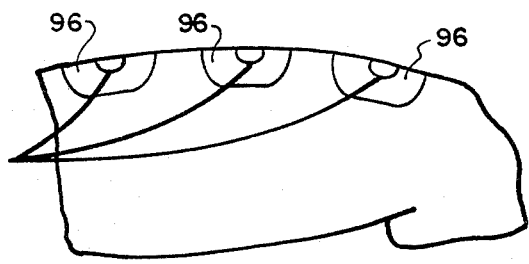
FIG. 8 is an elevational view showing placement of electrodes upon the leg of a chair occupant for stimulation.

The wheelchair 10 may be propelled by the legs of a paralyzed person through electrical stimulation of the leg muscles. As seen in FIG. 1, in such a case the wheelchair 10 includes a control box 90 mounted near one arm 92 of the wheelchair 10. The control box 90 is electrically connected to a stimulator 94, which provides electrical pulses to a series of electrodes 96, which are attached to the occupant's skin adjacent the muscles to be stimulated, namely, the quadriceps muscles of the legs. Electrodes 96 are commercially available transcutaneous electrodes such as MEDTRONIC Model 3793 electrodes sold by Medtronic, Inc. of Minneapolis, Minn. As shown in FIG. 8, three electrodes 96 are preferably attached to each leg, although any number of electrodes sufficient to provide adequate stimulation may be used. The electrodes 96 are attached to the legs by hypoallergenic tape or elastic bandages. Prior to application of the electrodes 96, the skin is cleaned and dried. An electrode gel, such as TENS electrode gel, also sold by Medtronic, Inc., is applied to the electrodes 96 before they are placed upon the skin of the chair occupant.

In one embodiment of the invention, the stimulator 94 may be a solid-state square pulse stimulator, such as a GRASS Model SD 9, manufactured by Grass Instrument Company of Quincy, Mass. The stimulator is used for simple on/off stimulation of the quadriceps muscles, controlled by a pair of push button switches 98 and 100 included in the control box 90. A multi-wire cable 102, shown in FIGS. 3 and 4, is used to convey wires from both control box 90 and the electrodes 96 to the stimulator 94, which is mounted at the rear of wheelchair 10 to frame portion 56 along with the necessary battery (not shown) for supplying power to stimulator 94.

Operation of the stimulation apparatus is commenced by depressing push button 98 of control box 90, as shown in FIG. 3. Stimulator 94 in response provides an output stimulation signal to the electrodes 96 attached to the right leg. The right quadriceps contracts whereby the lower leg and foot is extended outwardly, causing forward driving of the wheelchair 10 as has been described herein. Upon observing that the leg is fully extended, as shown in FIG. 4, the occupant of the chair releases pushbutton 98, whereupon stimulation of the quadriceps ceases. It will be recalled that the drive means 62 will now disengage from driving gear 60. Due to the slight incline of footrest 38, the right foot is then returned by gravity to its starting position. The occupant then depresses the second pushbutton 100, causing stimulation of the left quadriceps in a manner identical to that described for the right. Pushbutton 100 is released after full extension of the left lower leg, whereupon it is returned by gravity to its starting position.

Of course, it will be recognized that a number of other forms of apparatus for providing electrical stimulation for driving the wheelchair 10 may be used. A more complex and preferred apparatus uses a stimulator as disclosed in the above mentioned Petrofsky et al. application. In such an embodiment push buttons 98 and 100 supply ON/OFF analog control voltages to two separate pulse generating circuits, each being constructed as disclosed in Petrofsky et al. Each pulse generating circuit supplies a pair of alternatingly pulsed stimulation signals to the set of three electrodes 96 placed on one of the legs of the occupant as illustrated in FIG. 8. For such operation the center electrode 96 is connected to high voltage ground, and the two outside electrodes are active.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. A wheelchair comprising:
   a chair portion including a pair of upright frame members, a generally planar and horizontal seat and a generally planar and vertical back connected between said frame members for supporting the body of a disabled person, and an arm rest carried on each of said frame members;
   a chassis for supporting said chair portion;
   a pair of side wheels for supporting said chassis;
   at least one front wheel smaller than said side wheels for cooperating therewith in supporting said chassis;

a pair of individually movable footrests connected to said chassis for supporting the feet of said persons; and drive means connected to said footrests for propelling said wheelchair in response to movement of at least one of said footrests.

2. A wheelchair as defined in claim 1, wherein said drive means is further connected to said side wheels for propelling said wheelchair by driving movement of said side wheels.

3. A wheelchair as defined in claim 2, wherein each of said footrests are movable in response to extension and flexion of one of the legs of said person.

4. A wheelchair as defined in claim 3, wherein said drive means drives one of said side wheels in response to movement of one of said footrests caused by extension of one of the legs of said person.

5. A wheelchair comprising:

a chair portion including a pair of upright frame members, a generally planar and horizontal seat and a generaly planar and vertical back connected between said frame members for supporting the body of a disabled person, and an arm rest carried on each of said frame members;

a chassis for supporting said chair portion;

a pair of side wheels for supporting said chassis;

at least one front wheel smaller than said side wheels for cooperating therewith in supporting said chassis;

means for generating linear motion in response to extension and flexion of at least one of the legs of said person; and means for translating said linear motion into rotary movement for driving said wheelchair.

6. A wheelchair as defined in claim 5, wherein said linear motion generating means includes a pair of footrests for supporting the feet of said person, each of said footrests being individually linearally movable in response to extension and flexion of one of the legs of said person.

7. A wheelchair as defined in claim 6, further comprising means for supporting said footrests from said chassis, said supporting means including a pair of support plates and means slideably mounting one of said footrests to each of said plates.

8. A wheelchair as defined in claim 7, wherein said supporting means supports said footrests for linear motion in a first direction extending forwardly with respect to said chassis and in a second direction opposite said first direction.

9. A wheelchair as defined in claim 8, wherein said support plates are mounted so as to define an inclined planar suface such that movement of said footrests in said first direction is upwardly along the incline of said surface and movement of said footrests in said second direction is downwardly along said incline.

10. A wheelchair comprising:

a chair portion including a pair of upright frame members, a generally planar and horizontal seat and a generally planar and vertical back connected between said frame members for supporting the body of a disabled person, and an arm rest carried on each of said frame members;

a chassis for supporting said chair portion;

a pair of side wheels for supporting and driving said chassis;

at least one front wheel smaller than said side wheels for cooperating therewith in supporting said chassis;

a pair of individually movable footrests connected to said chassis for supporting the feet of said person;

a pair of driving gears, one of said gears being mounted for rotation concentrically and in conjunction with each of said side wheels;

means for engaging each of said driving gears for individual driving movement of said gears in a first rotational direction, and for non-engaging individual movement along said driving gears in a second rotational direction opposite said first direction; and means connecting said engaging means with said footrests such that individual movement of one of said footrests in a first linear direction causes said engaging means to move one of said driving gears in said first rotational direction, and movement of said footrest in a second linear direction opposite said first linear direction causes movement of said engaging means in said second, non-engaging rotational direction.

11. A wheelchair as defined in claim 10, wherein said engaging means includes a pair of levers, each of said levers being pivotally mounted for rotation concentric with but independent from one of said driving gears, a pair of pawls, one of said pawls being pivotally mounted on each of said levers, and means for pivotally moving each of said pawls for engagement with the corresponding one of said driving gears in response to movement of the one of said levers carrying the one of said pawls in said first rotational direction, and for disengagement from said gear in response to movement of said one of said levers in said second rotational direction.

12. A wheelchair as defined in claim 11, wherein said connecting means includes a pair of assemblies, each of said assemblies including an arm pivotally mounted to said chassis at a point along said arm remote from either end thereof, a first rod pivotally connected between a first end of said arm and one of said footrests, and a second rod pivotally connected between the end of said arm opposite said first end and one of said levers, movement of said footrest in said first linear direction causing said first rod to pivot said arm in one direction, said second rod thereby moving said lever in said first rotational direction, and movement of said footrest in said second linear direction causing said first rod to pivot said arm in a direction opposite said one direction, said second rod thereby moving said lever in said second rotational direction.

13. A wheelchair as defined in claim 12, wherein said means for pivotally moving each of said pawls includes a third rod pivotally mounted at one end thereof to said second rod, a linkage pivotally connected to the end of said third rod opposite said one end, said linkage being further pivotally mounted to said lever at the point of mounting of said pawl, and a friction pad disposed between said pawl and said linkage, said third rod, said linkage and said friction pad being operative to pivot said pawl into engagement with said driving gear in response to pivotal movement of said arm caused by movement of said footrest in said first linear direction, and to pivot said pawl out of engagement with said driving gear in response to pivotal movement of said arm caused by movement of said footrest in said second linear direction.

* * * * *